US00PP19114P2

(12) United States Plant Patent
Smith

(10) Patent No.: US PP19,114 P2
(45) Date of Patent: Aug. 19, 2008

(54) ***CHRYSANTHEMUM* PLANT NAMED 'ROSY YOIGLOO'**

(50) Latin Name: *Chrysanthemum×morifolium*
Varietal Denomination: Rosy Yoigloo

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/705,878

(22) Filed: Feb. 14, 2007

(51) Int. Cl.
*A01H 5/00* (2006.01)

(52) U.S. Cl. ..... Plt./298

(58) Field of Classification Search ..... Plt./298, Plt./286, 287, 293
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct of *Chrysanthemum* plant named 'Rosy Yoigloo', characterized by its upright, outwardly spreading and mounding plant habit; freely branching habit; dense and full plant habit; uniform and freely flowering habit; duplex-type inflorescences with obovate-shaped ray florets; red-colored ray florets; and natural season flowering about September 18$^{th}$ in the Northern Hemisphere.

1 Drawing Sheet

Botanical designation: *Chrysanthemum×morifolium.*
Cultivar denomination: 'ROSY YOIGLOO'.
Cross-reference to related application: *Chrysanthemum* Plant Named 'Warm Yoigloo'; U.S. Plant patent application Ser. No. 11/705,880; Mark A. Smith, Applicant; filed concurrently.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum* and hereinafter referred to by the name 'Rosy Yoigloo'.

The objective of the breeding program is to create new perennial garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Warm Yoigloo, disclosed in a U.S. Plant patent application filed concurrently. The new *Chrysanthemum* was discovered and selected by the Inventor as a single flowering plant within a population of plants of the cultivar Warm Yoigloo in December, 2003, in Alva, Fla. The selection of this plant was based on its desirable inflorescence color and good form and substance.

Asexual reproduction of the new *Chrysanthemum* by vegetative cuttings was first conducted in Alva, Fla. in February, 2004. Asexual reproduction by cuttings has shown that the unique features of this new *Chrysanthemum* are stable and reproduced true to type in successive generations.

SUMMARY OF THE INVENTION

Plants of the cultivar Rosy Yoigloo have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rosy Yoigloo'. These characteristics in combination distinguish 'Rosy Yoigloo' as a new and distinct garden *Chrysanthemum* cultivar:

1. Upright, outwardly spreading and mounding plant habit.
2. Freely branching habit; dense and full plant habit.
3. Uniform and freely flowering habit.
4. Duplex-type inflorescences with obovate-shaped ray florets.
5. Red-colored ray florets.
6. Natural season flowering about September 18$^{th}$ in the Northern Hemisphere.

In side-by-side comparisons conducted in Alva, Fla., plants of the new *Chrysanthemum* differed from plants of the parent, the cultivar Warm Yoigloo, in the following characteristics:

1. Plants of the new *Chrysanthemum* flowered later than plants of the cultivar Warm Yoigloo when grown under natural season conditions.
2. Plants of the new *Chrysanthemum* and the cultivar Warm Yoigloo differed in ray floret color as plants of the cultivar Warm Yoigloo had orange bronze-colored ray florets.

Plants of the new *Chrysanthemum* can be compared to plants of the *Chrysanthemum* cultivar MN 92-333-2, disclosed in U.S. Plant Pat. No. 14,197. In side-by-side comparisons conducted in Alva, Fla. plants of the new *Chrysanthemum* differed from plants of the cultivar MN 92-333-2 in the following characteristics:

1. Plants of the new *Chrysanthemum* were smaller, fuller and more mounted than plants of the cultivar MN 92-333-2.
2. Plants of the new *Chrysanthemum* had smaller inflorescences with more ray florets than plants of the cultivar MN 92-333-2.

3. Plants of the new *Chrysanthemum* flowered ten days earlier than plants of the cultivar MN 92-333-2 when grown under natural season conditions.
4. Ray floret color of plants of the new *Chrysanthemum* did not fade as quickly as ray floret color of plants of the cultivar MN 92-333-2.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Rosy Yoigloo'.

The photograph at the top of the sheet is a close-up view of typical inflorescences of 'Rosy Yoigloo'.

DETAILED BOTANICAL DESCRIPTION

The aforementioned photographs and following observations and measurements describe plants grown in Pendleton, S.C. during the summer in an outdoor nursery and under conditions and practices which approximate those generally used in commercial garden *Chrysanthemum* production. During the production of the plants, day temperatures averaged 32° C. and night temperatures averaged 21° C. Plants were grown in 20 cm containers under natural season conditions. Plants used in the photographs and for the description were about four months old. In the following description, color references are made to The Royal Horticultural Society Colour Chart, 1995 Edition, except where general terms of ordinary dictionary significance are used.

Botanical classification: *Chrysanthemum×morifolium* cultivar Rosy Yoigloo.

Parentage: Naturally-occurring whole plant mutation of the *Chrysanthemum×morifolium* cultivar Warm Yoigloo, disclosed in a U.S. Plant Patent application filed concurrently.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial duplex-type garden *Chrysanthemum*. Stem upright and outwardly spreading giving a uniformly mounded appearance to the plant. Freely branching habit, about eight lateral branches each with multiple secondary and tertiary branches; pinching is not required; dense and full plant habit. Strong and vigorous growth habit.

*Plant height.*—About 29 cm.

*Plant width.*—About 57 cm.

*Lateral branches.*—Length: About 30 cm. Diameter: About 9 mm. Internode length: About 1.5 cm to 2.5 cm. Strength: Strong. Texture: Pubescent. Color: 148A to 148B.

*Leaves.*—Arrangement: Alternate, simple. Length: About 4 cm. Width: About 2.4 cm. Apex: Acuminate. Base: Attenuate. Margin: Palmately lobed, sinuses between lateral lobes mostly convergent. Texture, upper and lower surfaces: Pubescence; veins prominent on lower surface. Color: Developing foliage, upper surface: 147A. Developing foliage, lower surface: Darker than 147B. Fully expanded foliage, upper surface: 137A; venation, 137B. Fully expanded foliage, lower surface: 138B; venation, 138B. Petiole: Length: About 6 mm. Diameter: About 3 mm. Texture, upper and lower surfaces: Pubescent. Color, upper surface: 138A. Color, lower surface: 148C.

Inflorescence description:

*Appearance.*—Duplex-type inflorescence form with obovate-shaped ray florets. Inflorescences borne on terminals above foliage. Disk and ray florets arranged acropetally on a capitulum. Inflorescences fragrant, typical of *Chrysanthemum*.

*Flowering response.*—Under natural season conditions, plants flower about September 18$^{th}$ in the Northern Hemisphere.

*Postproduction longevity.*—Inflorescences maintain good color and substance for about four weeks in an outdoor nursery. Inflorescences persistent.

*Quantity of inflorescences.*—About 100 inflorescences develop per lateral branch.

*Inflorescence bud.*—Height: About 9 mm. Diameter: About 1.4 cm. Shape: Oblate. Color: 183C.

*Inflorescence size.*—Diameter: About 3.5 cm. Depth (height): About 1.7 cm. Disc diameter: About 4 mm. Receptacle height: About 4 mm. Receptacle diameter: About 1.5 cm.

*Ray florets.*—Shape: Obovate. Orientation: Initially upright, then about 90° from vertical; eventually reflexing. Aspect: Initially incurved, then mostly flat. Length: About 1.6 cm. Width: About 4 mm. Apex: Emarginate. Base: Acute. Margin: Entire. Texture, upper and lower surfaces: Smooth, glabrous; longitudinally ribbed. Number of ray florets per inflorescence: About 170 arranged in about 14 to 15 whorls. Color: When opening, upper surface: 185A to 185B. When opening, lower surface: 173D. Fully opened, upper surface: 180A; color becoming closer to 178D with development. Fully opened, lower surface: 173C to 173D; color becoming closer to 165C with development.

*Disc florets.*—Shape: Tubular, elongated. Length: About 3 mm. Diameter: Less than 1 mm. Number of disc florets per inflorescence: About 116. Color, immature. Apex: Close to 14A. Mid-section: Close to 14C. Base: Close to 2A. Color, mature: Apex: Close to 14A. Mid-section: Close to 14D. Base: Close to 2A.

*Phyllaries.*—Number of phyllaries per inflorescence: About 24 arranged in about five whorls. Length: About 6 mm. Width: About 2 mm. Shape: Elliptical. Apex: Acute. Base: Truncate. Texture, upper surface: Smooth, glabrous. Texture, lower surface: Pubescent. Color, upper surface: Close to 147C. Color, lower surface: Close to 147B.

*Peduncles.*—Length: About 5.5 cm. Diameter: About 1 mm. Angle: Mostly upright or curving upright. Strength: Strong. Texture: Pubescent. Color: Close to 148C.

*Reproductive organs.*—Androecium: None observed on disc florets. Gynoecium: Present on both ray and disc florets. Pistil length: About 4 mm. Stigma shape: Bi-parted. Stigma color: Close to 10A. Style length: About 2 mm. Style color: Close to 10D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Rosy Yoigloo' as illustrated and described.

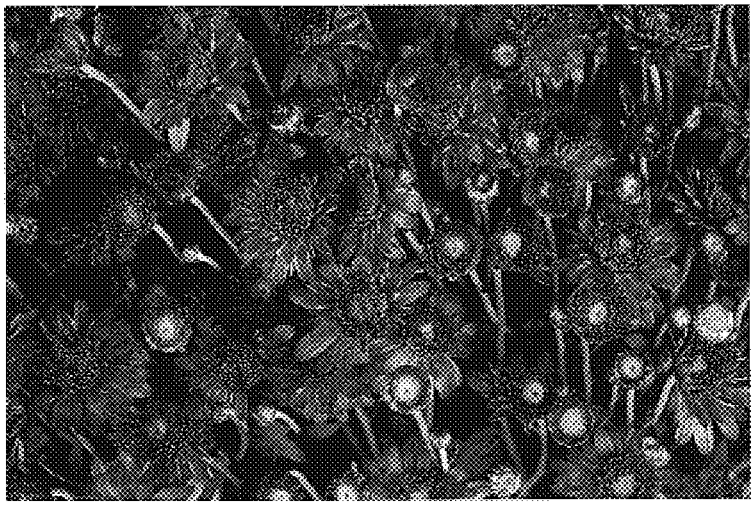
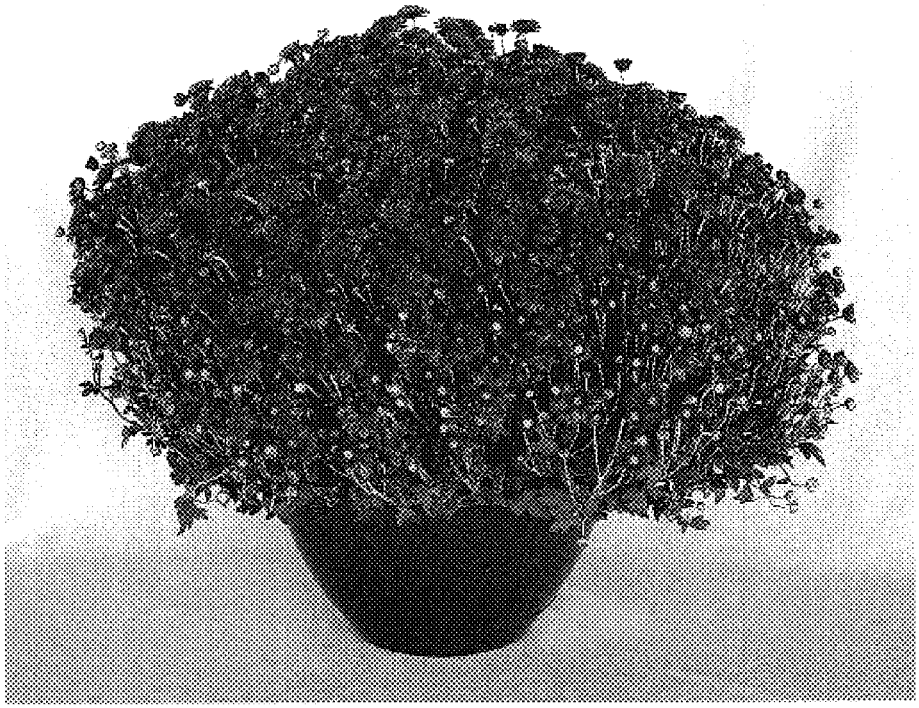

* * * * *